United States Patent
Deslauriers et al.

(10) Patent No.: US 8,852,199 B2
(45) Date of Patent: Oct. 7, 2014

(54) METHOD AND DEVICE FOR HANDLING BONE ADHESIVES

(75) Inventors: Richard J. Deslauriers, Woodbury, CT (US); Steven Joseph Beer, Cheyenne, WY (US); Eric Kolb, Sandy Hook, CT (US); Joseph Jannetty, Naugatuck, CT (US)

(73) Assignee: ABYRX, Inc., Irvington, NY (US)

( * ) Notice: Subject to any disclaimer, the term of this patent is extended or adjusted under 35 U.S.C. 154(b) by 601 days.

(21) Appl. No.: 12/852,260

(22) Filed: Aug. 6, 2010

(65) Prior Publication Data
US 2012/0035610 A1 Feb. 9, 2012

(51) Int. Cl.
*A61B 17/58* (2006.01)
*A61B 17/00* (2006.01)
*A61B 19/04* (2006.01)

(52) U.S. Cl.
CPC ..... *A61B 17/00491* (2013.01); *A61B 2019/043* (2013.01)
USPC .............................. 606/93; 606/86 R; 606/92

(58) Field of Classification Search
USPC .......................... 606/86 R, 92–94; 623/16.11, 623/17.17–17.19, 23.48–23.63
See application file for complete search history.

(56) References Cited

U.S. PATENT DOCUMENTS

| | | | | |
|---|---|---|---|---|
| 4,477,604 A | * | 10/1984 | Oechsle, III | 523/116 |
| 4,777,186 A | * | 10/1988 | Stang et al. | 521/50 |
| 5,501,706 A | * | 3/1996 | Arenberg | 623/23.56 |
| 5,638,701 A | | 6/1997 | Dempsey | |
| 5,947,123 A | | 9/1999 | Shippert | |
| 5,957,690 A | * | 9/1999 | Bartee et al. | 433/215 |
| 6,328,765 B1 | * | 12/2001 | Hardwick et al. | 623/23.72 |
| 7,044,982 B2 | | 5/2006 | Milbocker | |
| 2005/0220771 A1 | | 10/2005 | Deslauriers et al. | |
| 2011/0015743 A1 | * | 1/2011 | Deslauriers et al. | 623/17.16 |

OTHER PUBLICATIONS

"Bonding low surface energy plastics", <http://machinedesign.com/article/bonding-low-surface-energy-plastics-0615>, Jun. 15, 2000, Penton Media, Inc., Mar. 29, 2010.

* cited by examiner

*Primary Examiner* — Nicholas Woodall
(74) *Attorney, Agent, or Firm* — Mintz Levin Cohn Ferris Glovsky and Popeo, P.C.; Muriel Liberto, Esq.

(57) ABSTRACT

A bone adhesive application device has a pliable structure with an application surface upon which a bone adhesive may be applied. The application surface has a surface energy substantially equal to or less than a surface energy of the bone adhesive to reduce adhesion between the bone adhesive and the bone adhesive application device. The bone adhesive application device may be included in a kit for repairing bone defects having a bone adhesive formed from a reactive biocompatible polyurethane material. The bone adhesive may be applied to a bone defect by positioning the pliable structure over at least a portion of the bone defect, delivering the bone adhesive to the bone defect and removing the pliable structure from the bone adhesive.

18 Claims, 5 Drawing Sheets

METHOD AND DEVICE FOR HANDLING BONE ADHESIVES

FIELD OF THE INVENTION

The present invention relates to bone adhesive and, more particularly, to the handling of bone adhesives.

BACKGROUND OF THE INVENTION

There are many situations in which defects in bones or portions of bones must be repaired or replaced, including fractures, joint degeneration, abnormal bone growth, infection and the like. For instance, a bone fracture may result in a crack that must be filled or in a portion of missing bone that must be replaced. Similarly, an infection may result in the removal of a portion of bone also requiring replacement.

Conventional bone replacement technologies have developed bone defect fillers for repairing bones by filling bone voids, gaps, cracks and the like. For instance, synthetic bone defect fillers, which are resorbable and porous, may replace bone with a bone-like mineral, e.g. crystalline hydroxyapatite or tricalcium phosphate. The resorbable and porous properties of these synthetic bone defect fillers allow for bone remodeling following implantation. However, conventional synthetic bone defect fillers are problematic because they may have poor tensile strength, flexural and sheer properties and they adhere poorly to the surrounding bone, which can result in washout of the bone defect filler from the bone defect prior to ingrowth of new bone into the bone defect filler.

Another conventional bone replacement technology includes bone defect fillers with a composition that maintains its chemical and mechanical properties without change or subsequent remodeling. For instance, metallic and PEEK implants may be used as interbody spacers for spinal fusion. However, these permanent bone defect fillers are problematic because, inter alia, they are not resorbable, cannot be molded and shaped for in situ curing and do not provide for adhesion with surrounding bone. Some conventional bone replacement fillers, such as PMMA, do allow for a limited amount of shaping prior to solidification. However, the time during which these conventional fillers may be shaped is relatively small, providing a surgeon with a very limited window in which the bone filler must be implanted. Additionally, like the metallic and PEEK implant described previously, these bone fillers are not resorbable and do not provide chemical adhesion between the bone and the bone defect filler.

Polymeric bone adhesives have more recently been developed for filling and/or repairing bone defects. These polymeric bone adhesives are typically initially prepared in a liquid state that is chemically adhesive. As they cure, the polymeric bone adhesives become more viscous and slowly diminish in their chemically adhesive characteristics until the polymeric bone adhesives polymerize into a final solid state. These polymeric bone adhesives may advantageously be applied to the bone defect early during the polymerization process and may be molded, shaped and allowed to cure in situ to provide both chemical and mechanical adhesion with the bone surrounding the bone defect. Thus, polymeric bone adhesives may provide improved tensile strength and adhesive characteristics over other conventional synthetic bone defect fillers. Additionally, polymeric bone adhesives may be formed with a porous structure for promoting new bone ingrowth. However, the chemically adhesive characteristics of these polymeric bone adhesives may make the polymeric bone adhesives more difficult to apply to bone defects using conventional application tools since the polymeric bone adhesives may unintentionally adhere to undesirable surfaces and/or elements contacted during handling and delivery, such as a surgeon's gloves, bone adhesive holding containers, surgical implantation instruments or the like. Additionally, if the polymeric bone adhesives are applied to the bone defect while substantially liquid, they may have a tendency to fall/run out of the application site. Care must also be taken while curing some polymeric bone adhesives to avoid contamination, which can lead to expansion, decreased adhesive characteristics and/or decreased mechanical strength.

Current solutions for handling bone adhesives include dipping the surgical gloves and/or instruments in a liquid solution, such as saline, blood or fat, prior to contact with the bone adhesive. The liquid solution is effective in reducing adhesion between the bone adhesive and the surgical gloves and/or instruments. However, the liquid solution may adversely affect the polymerization of the bone adhesive by reducing the adhesive strength at the interface between the bone and the bone adhesive within the bone defect. Additionally, the liquid solution may act as a contaminant to the bone adhesive adversely affecting the polymerization chemistry, causing excessive expansion during polymerization and/or degradation in mechanical properties by reducing the density of the bone adhesive and reducing cross-linking of polymer chains forming the bone adhesive.

Another solution for handling bone adhesives is to delay contact with the bone adhesive until the bone adhesive has partially polymerized to a degree at which its adhesiveness has lessened. However, while this technique is effective at reducing the tendency of the bone adhesive to adhere to the undesirable surfaces, such as instruments and/or gloves, it also reduces desirable adhesion between the bone adhesive and the bone surrounding the bone defect.

In some applications, bone adhesives may be applied through a syringe while in a liquid state to avoid adhesion to undesirable surfaces. However, while this technique eliminates contact with the bone adhesive, it does not allow for manipulation and/or shaping of the bone adhesive after the bone adhesive has been applied to the bone defect. Thus, the bone adhesive may lose its intended shape and/or flow out of the bone defect.

Accordingly, there is a need for a device providing improved handling, expansion and contamination characteristics for bone adhesives that overcomes the deficiencies of the prior art.

SUMMARY OF THE INVENTION

According to the present invention, a bone adhesive application device has a structure that may be pliable or rigid with an application surface upon which a bone adhesive may be applied. The application surface has a surface energy substantially equal to or less than a surface energy of the bone adhesive to reduce adhesion between the bone adhesive and the bone adhesive application device. In some embodiments, the pliable structure may be formed from a material having a low surface energy in the form of a thin sheet. In some embodiments, the application surface may include a surface coating that reduces the surface energy.

According to the present invention, the pliable structure of the bone adhesive application device may additionally include a manipulation surface through which a user may manipulate the bone adhesive without directly contacting the bone adhesive.

According to the present invention, the bone adhesive application device may be formed in a variety of shapes for different applications. In one embodiment, the pliable structure forms a sleeve having an outer application surface and an inner manipulation surface surrounding an internal cavity adapted to accommodate a finger of a user. In another embodiment, the pliable structure forms a container having an internal application surface and an external manipulation surface. In a further embodiment, the application surface includes at least one mold cavity formed therein. In another embodiment, the structure of the bone adhesive application device is rigid and includes a handle connected thereto.

According to the present invention, the pliable structure may also be formed in a preset shape that maintains its position on a bone. In one embodiment, the pliable structure may be formed to be substantially tubular.

According to the present invention, a kit for repairing bone defects includes a bone adhesive having a first surface energy and a bone adhesive application device having an application surface with a second surface energy. The second surface energy of the application surface may be lower than the first surface energy of the bone adhesive to reduce adhesion between the bone adhesive and the bone adhesive application device. The bone adhesive of the kit may be a reactive biocompatible polyurethane material.

According to the present invention, a method for applying bone adhesive includes positioning a pliable structure with an application surface over at least a portion of the bone defect, delivering the bone adhesive to the bone defect and removing the pliable structure from the bone adhesive. The surface energy of the application surface may be lower than the surface energy of the bone adhesive to reduce adhesion between the bone adhesive and the pliable structure.

According to the present invention, the method for applying bone adhesive may also include shaping the bone adhesive. In some embodiments, the bone adhesive may be manipulated through a manipulation surface of the pliable structure.

According to the present invention, the bone adhesive may be delivered directly to the bone defect or deposited on the application surface of the pliable structure and then delivered to the bone defect. In some embodiments, the bone adhesive may be deposited in a mold cavity of the application surface.

These and other objects, features and advantages of the present invention will become apparent in light of the following detailed description of non-limiting embodiments, with reference to the accompanying drawings.

DETAILED DESCRIPTION OF A PREFERRED EMBODIMENT

Figure 1A:
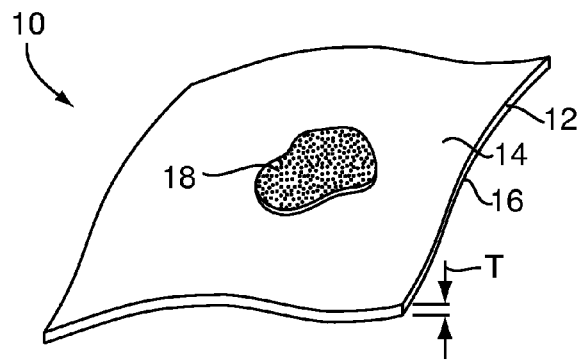
FIG. 1A is a perspective view of a low surface energy sheet according to an embodiment of the present invention.

Referring to FIG. 1A, a bone adhesive application device in the form of a low surface energy (LSE) sheet 10 includes a pliable structure 12 having an application surface 14 and a manipulation surface 16. The pliable structure 12 has thickness T that may be varied depending upon the desired degree of flexibility of the pliable structure 12, as will be discussed in greater detail below. The application surface 14 is adapted to receive a bone adhesive 18, which is to be applied to a bone defect 20, shown in FIG. 1B, in a patient's bone 21, shown in FIG. 1B. The bone adhesive 18 is preferably formed from a reactive biocompatible polymeric material, which has adhesive characteristics to provide a bond with the bone 21, shown in FIG. 1B. The LSE sheet 10 improves handling of the adhesive bone adhesive 18, so that the bone adhesive 18 may be more readily applied to the bone defect 20, shown in FIG. 1B.

As discussed above, the bone adhesive 18 is preferably a reactive biocompatible polymeric material, which has adhesive characteristics. Additionally, the bone adhesive 18 is preferably osteoconductive when used in medical procedures. An example of one suitable reactive biocompatible polymeric material for the bone adhesive 18 is the KRYPTONITE™ bone matrix product, available from DOCTORS RESEARCH GROUP, INC. of Southbury, Conn., which is described in U.S. patent application Ser. No. 11/089,489, which is hereby incorporated by reference in its entirety.

Figure 2:
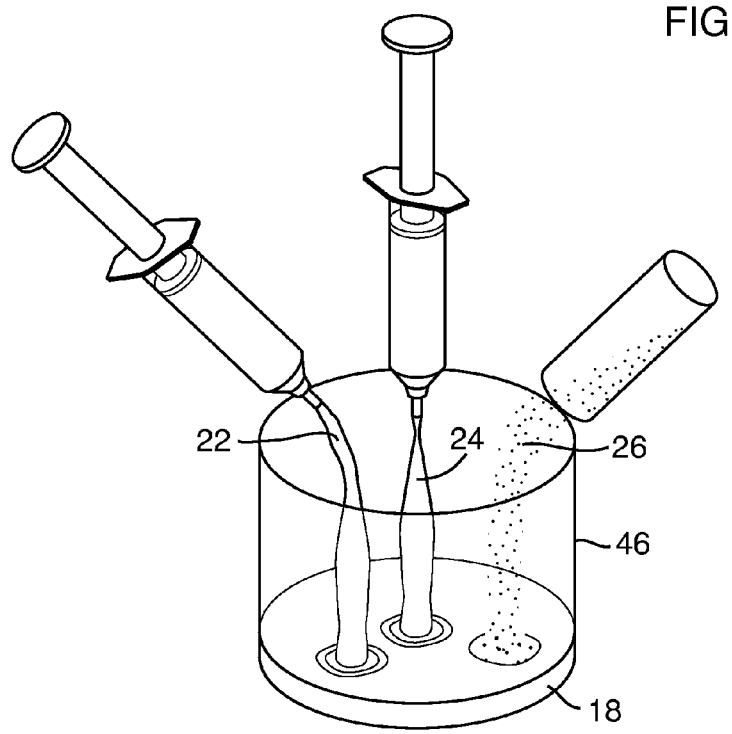
FIG. 2 is a perspective view of an embodiment for forming a bone adhesive according to the present invention.

Referring to FIG. 2, in some embodiments, the bone adhesive 18 may be formed by combining a prepolymer component 22 and a polyol component 24, along with an optional filler material 26, and permitting the combination to react to form the biocompatible polyurethane material of the bone adhesive 18.

The prepolymer component 22 for forming the bone adhesive 18 includes prepolymer molecules formed by reacting diisocyanate with polyol. The prepolymer component 22 may be a true prepolymer, formed with a two to one ratio of diisocyanate to polyol, or the prepolymer component 22 may be a quasi-prepolymer, formed with a ratio of diisocyanate to polyol in excess of two to one. As will be understood by those skilled in the art, a broad variety of diisocyanates and polyols may be suitable for use in the prepolymer component 22 and the bone adhesive 18 of the present invention. Both aromatic and aliphatic diisocyanates may be used to form the prepolymer component 22 of the present invention. The polyol used to form the prepolymer component may be the same as or different than the polyol of the polyol component 24. Additionally, the polyol used to form the prepolymer component 22 may be a blend of different polyols to achieve desired properties. Various polyols suitable for synthesis with the diisocyanate will be discussed in greater detail below.

The polyol component 24 for forming the bone adhesive 18 may include naturally occurring polyols and biocompatible, synthetic polyols, and mixtures thereof to achieve desired properties in the bone adhesive 18. The polyol component 24 preferably also includes a catalyst for controlling and/or reducing the time required for polymerization of the bone adhesive 18. Additionally, the polyol component 24 may include water, which is known to react with diisocyanate to produce carbon dioxide. Thus, the water may be provided to react with the diisocyanate to generate a sufficient amount of carbon dioxide to impart a degree of porosity to the bone adhesive 18. Alternatively, rather than including water in the polyol component 24, moisture from the atmosphere or moisture included in the optional filler material 26 may impart the degree of porosity to the bone adhesive 18. Additionally, in instances where moisture is provided from the atmosphere or within the optional filler material 26, it may be desirable to dry the polyols to provide improved control over the amount of carbon dioxide produced and, therefore, the degree of porosity imparted to the bone adhesive 18.

The optional filler material 26 for forming the bone adhesive 18 may include, but is not limited to, calcium carbonate, bone (e.g., demineralized bone, allograft bone, and/or autogenous bone), calcium phosphate, calcium pyrophosphate, hydroxyapatite, poly methyl methacrylate, glass-ionomer, calcium sulfate, tricalcium phosphate (e.g., beta tricalcium phosphate), or any combination thereof, or the like. In certain embodiments, the filler material 26 may be chosen so as to impart a desired degree of porosity to the bone adhesive 18. For example, the filler material 26 may include water for reacting with the diisocyanate of the prepolymer component 22 to generate carbon dioxide and impart the porosity to the bone adhesive 18. The filler material 26 may also be present in the bone adhesive 18 in an amount sufficient to modify the bone adhesive's mechanical properties (e.g., compressive strength, compressive modulus, Young's Modulus of Elasticity, flexural strength, and the like). The filler material 26 may also comprise calcium carbonate and, in certain of these embodiments, the filler material 26 may comprise calcium carbonate in an amount sufficient to provide free calcium to a body of a mammal and enhance osteoconductivity.

Although the bone adhesive 18 may be formed with a variety of compositions to achieve desired properties, preferably, the bone adhesive 18 is a biocompatible polyurethane material, wherein the prepolymer component 22 includes aromatic pMDI diiscyanates synthesized with polyols derived from castor oil. The polyol component 24 preferably also includes polyols derived from castor oil and a small percentage of catalyst. The optional filler material 26 is preferably calcium carbonate powder, at a concentration of thirty percent (30%) by weight, with approximately ninety percent (90%) of the powdered particles being less than ten microns (10 μm) in diameter.

The bone adhesive 18 is initially prepared in a liquid state when the prepolymer component 22, polyol component 24 and optional filler material 26 are combined. The bone adhesive 18 is chemically adhesive in this liquid state. As the bone adhesive 18 cures, it passes through a taffy-like state, in which the bone adhesive 18 is still chemically adhesive and is also easily malleable and may be shaped and sculpted to a desired geometry. The biocompatible polymeric material then passes into a putty-like state in which the material's adhesive properties are reduced and the material is easily malleable and may be shaped and sculpted. The bone adhesive 18 then cures into a final solid state. As the bone adhesive 18 cures, it becomes more viscous and less adhesive, i.e., the bone adhesive 18 loses tackiness, which, as used herein, is defines as the ability of the bone adhesive 18 to be slightly adhesive or gummy to the touch or to adhere to a dry surgical instrument, for example, a freer.

Figure 1B:
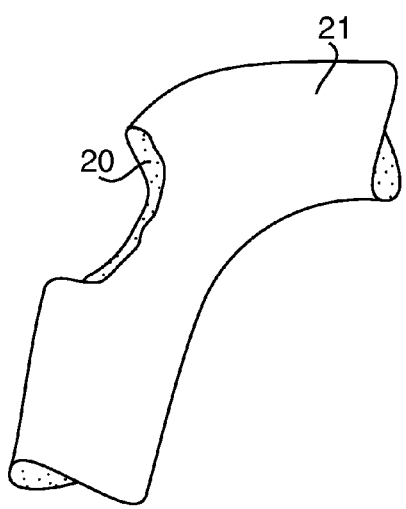
FIG. 1B is a side view of a bone defect that may be filled according to an embodiment of the present invention.

Since the adhesive properties of the bone adhesive 18 are greatest when the material is in the liquid or taffy-like state, the bone adhesive 18 is preferably in either the liquid state or the taffy-like state when applied to the bone defect 20, shown in FIG. 1B. Then, when the bone adhesive 18 is fully cured, an adhesive bond will have been formed with the bone 21, shown in FIG. 1B, surrounding the bone defect 20, shown in FIG. 1B. Additionally, the cured bone adhesive 18 may have a porous structure that is osteoconductive.

Figure 3:
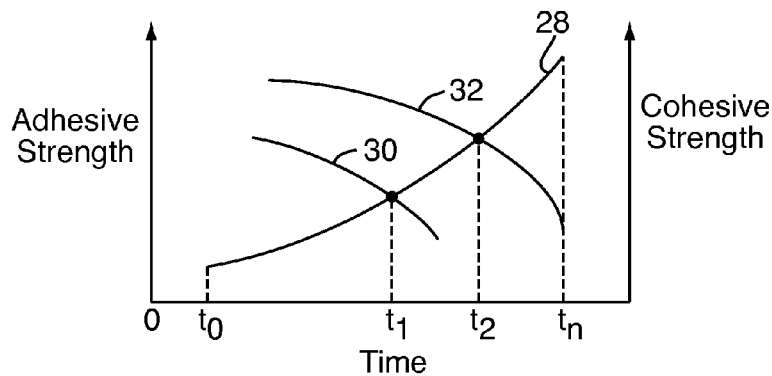
FIG. 3 is a line graph showing a reduction in adhesive strength provided by the low surface energy sheet of FIG. 1A.

Referring to FIG. 3, when the bone adhesive 18, shown in FIG. 2, is initially mixed at time $t_0$, a cohesive strength 28 of the bone adhesive 18, shown in FIG. 2, is relatively low. As the bone adhesive 18, shown in FIG. 2, cures from the liquid state to the fully cured solid state, the cohesive strength 28 increases until it reaches its final value when the bone adhesive 18, shown in FIG. 2, has fully cured at time $t_n$.

The LSE sheet 10, shown in FIG. 1A, improves handling of the bone adhesive 18, shown in FIG. 1A, while chemically adhesive, e.g., while in the liquid or taffy-like states discussed above. In particular, the LSE sheet 10 reduces adhesion between the bone adhesive 18, shown in FIG. 1A, and the application surface 14, shown in FIG. 1A, such that the cohesive strength 28 of the bone adhesive 18, shown in FIG. 1A, overcomes the adhesion between the bone adhesive 18, shown in FIG. 1A, and the application surface 14, shown in FIG. 1A. To do so, the LSE sheet 10, shown in FIG. 1A, is formed such that an LSE adhesive strength 30 of the bond formed between the bone adhesive 18, shown in FIG. 1A, and the application surface 14, shown in FIG. 1A, is reduced relative to a conventional adhesive strength 32 of the bond that would be formed between the bone adhesive 18 and a conventional application device (not shown), such as a surgical glove, bone adhesive holding containers, surgical implantation instruments or the like. This reduction in the LSE adhesive strength 30 results in a lower release time $t_1$ at which the cohesive strength 28 of the bone adhesive 18, shown in FIG. 1A, becomes greater than the LSE adhesive strength 30 as compared to a conventional release time $t_2$ at which the cohesive strength 28 of the bone adhesive 18, shown in FIG. 1A, becomes greater than the conventional adhesive strength 32. This reduction in the release time $t_1$ is particularly beneficial since the release time $t_1$ is the time at which the LSE sheet 10 may be removed from the bone adhesive 18 without substantially disturbing the bone adhesive 18, i.e., the time prior to full polymerization that the bone adhesive 18, shown in FIG. 1A, is cured enough that it is of sufficient cohesive strength 28 to substantially hold its own shape. Thus, by reducing the LSE adhesive strength 30 relative to the conventional adhesive strength 32, the LSE sheet 10, shown in FIG. 1A, may more readily be removed from the bone adhesive 18, shown in FIG. 1A, after the bone adhesive 18, shown in FIG. 1A, has been delivered to the bone defect 20, shown in FIG. 1B, and prior to full polymerization, without disturbing the bone adhesive 18, shown in FIG. 1A, due to adhesion with the LSE sheet 10, shown in FIG. 1A.

Referring back to FIG. 1A, the LSE sheet 10 minimizes the LSE adhesive strength 30, shown in FIG. 3, of the bond formed between the bone adhesive 18 and the application surface 14 by minimizing a degree of wetting of the application surface 14. The degree of wetting of the application surface 14 depends upon the ability of the bone adhesive 18 to spread across the application surface 14 and to penetrate into surface features, i.e., surface roughness, of the application surface 14 when the bone adhesive 18 is deposited on the application surface 14. The LSE sheet 10 is able to minimize spreading of the bone adhesive 18 across the application surface 14 by providing the application surface 14 with a low surface energy. For instance, as seen in Table 1, the LSE sheet 10 may be formed with a low surface energy from a variety of materials including polytetrafluorotheylene (PTFE), e.g., Teflon®, polypropylene, polyethylene terephthalate (PET) and/or polystyrene. Most preferably, the LSE sheet 10 is formed from silicone.

TABLE 1

Relative Surface Energies
RELATIVE SURFACE ENERGIES

| SURFACE | SURFACE ENERGY (Dynes/cm) |
|---|---|
| Copper | 1,103 |
| Aluminum | 840 |
| Glass | 250 to 500 |
| HIGH SURFACE ENERGY PLASTICS | |
| Kapton (DuPont) | 50 |
| Polyurethane | 43 |
| ABS | 42 |
| Polycarbonate | 42 |
| LOW SURFACE ENERGY PLASTICS | |
| Polystyrene | 36 |
| Polyethylene | 31 |
| Polypropylene | 29 |
| Silicone | 24 |
| Teflon (DuPont) | 18 |

(See "Machine Design." *Bonding low surface energy plastics*. Jun. 15, 2000. Penton Media, Inc. Mar. 26, 2010. <http://machinedesign.com/article/bonding-low-surface-energy-plastics-0615>)

Forming the LSE sheet 10 from a material having a low surface energy results in an application surface 14 with a low surface energy, which as discussed above, minimizes spreading of the bone adhesive 18 on the application surface 14, thereby reducing the degree of wetting of the application surface 14. Thus, the LSE sheet 10 weakens the adhesive strength 22, shown in FIG. 2, of the resulting adhesive bond formed between the bone adhesive 18 and the application surface 14 of the LSE sheet 10.

As seen in Tables 1 and 2, PTFE, silicone and polypropylene have surface energies lower than reactive polyurethanes, i.e. the reactive biocompatible polyurethane material forming the bone adhesive 18, and polystyrene has substantially the same surface energy as reactive polyurethanes. Thus, these materials are preferable for forming the LSE sheet 10.

TABLE 2

Relative Surface Energies of Plastics and Adhesives

| | LSE (Low Surface Energy) | | | | HSE (High Surface Energy) | | | |
|---|---|---|---|---|---|---|---|---|
| | PTFE | Silicone | Polypropylene | Polystyrene | Acrylic | PVC | ABS | Polyester |
| STRUCTURAL ADHESIVES | | | Two-part Acrylic | Two-part Epoxy Two-part Urethane | | | | |
| | | Cyanoacrylate (CA) Rite-Lok ™ Cyanoacrylate Primer | | Polyurethane Reactive (PUR) | | | | |

In addition to reducing wetting of the application surface 14 by forming the LSE sheet 10 from a material having a low surface energy, the degree of wetting may also be reduced by controlling the penetration of the bone adhesive 18 into the application surface 14. For instance, in some embodiments, the bone adhesive 18 may be deposited on the application surface 14 in a more viscous state to reduce penetration of the bone adhesive 18 into the application surface 14. In some embodiments, a surface texture of the application surface 14 of the LSE sheet 10 may also be formed to manipulate the degree of wetting of the application surface 14. For instance, the application surface 14 may be formed to be relatively smooth to reduce wetting. Alternatively, a surface texture on the micrometer or nanometer scale may be imparted on the application surface 14 to minimize wetting.

Figure 4:
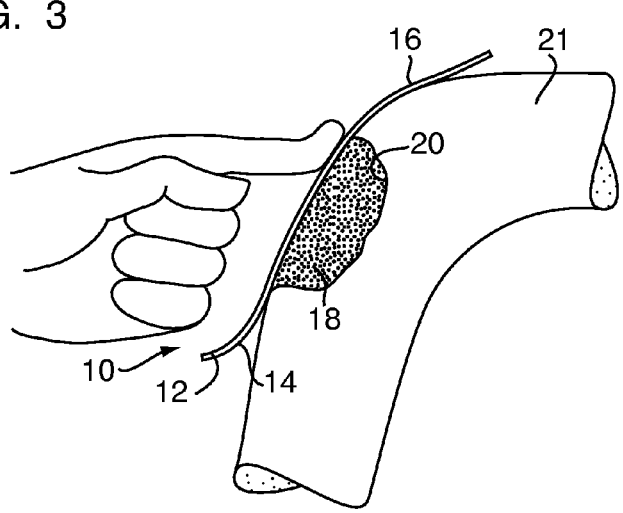
FIG. 4 is a side view of bone adhesive being applied to a bone defect using the low surface energy sheet of FIG. 1A.

Referring to FIG. 4, in operation, a user may prepare the bone adhesive 18, for example, by mixing the prepolymer component 22, the polyol component 24 and the filler material 26, shown in FIG. 2, at time $t_0$, shown in FIG. 3. Then, the user may deliver the bone adhesive 18 to the bone defect 20 and bring the LSE sheet 10 into contact with the bone adhesive 18 and bone 21 to contain the bone adhesive 18 within the bone defect 20 and/or to manipulate the shape of the bone adhesive 18.

The user may hold the LSE sheet 10 by the manipulation surface 16 to contain the bone adhesive 18 within the bone defect 20. Due to the flexible nature of the LSE sheet 10, the user may also manipulate and/or shape the bone adhesive 18 to a desired shape through the manipulation surface 16 of the LSE sheet 10, for example, by pushing on the manipulation surface 16. Thus, the user is able to both maintain the bone adhesive 18 within the bone defect 20 and to manipulate the bone adhesive 18 to a desired shape in situ, without directly contacting the bone adhesive 18. In some embodiments, the LSE sheet 10 may be formed to be substantially transparent to allow the user to visualize the bone defect 20 and bone adhesive 18 during application and manipulation.

Once the bone adhesive 18 has been manipulated to the desired shape, the user may wait until the release time $t_1$, shown in FIG. 3, before removing the LSE sheet 10 from the bone adhesive 18. As the user waits for the release time $t_1$, shown in FIG. 3, the bone adhesive 18 cures within the bone defect 20 and the cohesive strength 28, shown in FIG. 3, of the bone adhesive 18 increases. Additionally, the adhesive strength of the bond between bone adhesive 18 and the bone 21 surrounding the bone defect 20 increases as the bone adhesive 18 cures. Advantageously, the LSE sheet 10 may act as a barrier while the bone adhesive 18 is curing to prevent contaminants from mixing with the bone adhesive and adversely affecting the polymerization process.

Figure 5:
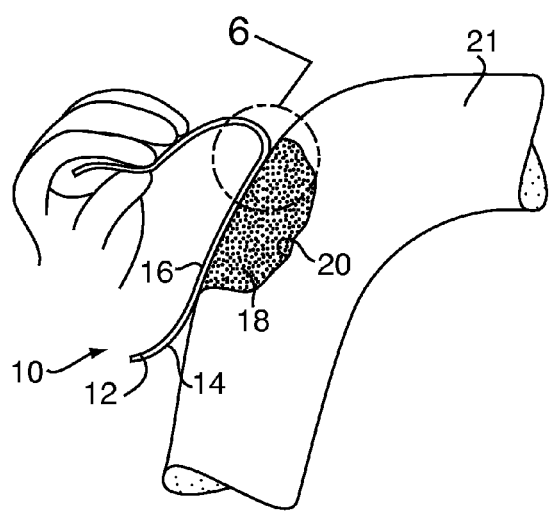
FIG. 5 is a side view of the low surface energy sheet of FIG. 4 being released from the bone adhesive within the bone defect.

Referring to FIG. 5, once the release time $t_1$, shown in FIG. 3, has been reached, the LSE sheet 10 may be peeled away from the bone adhesive 18. As the LSE sheet 10 is peeled away, the bone adhesive 18 is left substantially intact, since the cohesive strength 28, shown in FIG. 3, of the curing bone adhesive 18 is at least substantially equal to or greater than the LSE adhesive strength 30, shown in FIG. 3, of the adhesive bond between the bone adhesive 18 and the LSE sheet 10. Once the LSE sheet 10 is removed, the bone adhesive 18 continues to cure within the bone defect 20 until time $t_n$, shown in FIG. 3, at which point the bone adhesive 18 is fully cured and an adhesive bond with the bone 21 surrounding the bone defect 20 has been formed.

Since the LSE sheet 10 provides for an earlier release time $t_1$, shown in FIG. 3, than conventional application devices, the LSE sheet advantageously reduces the likelihood of premature removal, which could disrupt the bone adhesive 18. This earlier release time $t_1$, shown in FIG. 3, may also result in reduced operating room time for performing bone repair surgeries, resulting in significant time and cost savings.

Although application of the bone adhesive 18 has been described as first having the bone adhesive 18 deposited within the bone defect 20 and then having the LSE sheet 10 brought into contact with the bone adhesive 18, in other embodiments, the bone adhesive may be first deposited on the LSE sheet 10, where the bone adhesive 18 may be shaped and/or manipulated. Then, the user may bring the LSE sheet 10, with the bone adhesive 18 thereon, into contact with the bone defect 20 to deliver the bone adhesive 18 to the bone defect 20. The user may then further manipulate the shape of the bone adhesive 18, if necessary.

Figure 6:
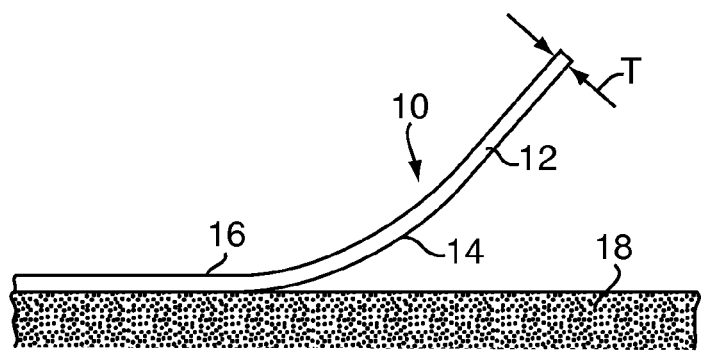
FIG. 6 is an enlarged side view of the low surface energy sheet being released from the bone adhesive of FIG. 5.

Referring to FIG. 6, as discussed above, the thickness T of the LSE sheet 10 may be selected to impart a desired flexibility to the LSE sheet 10. For instance, a thinner LSE sheet 10 may better facilitate manipulation of the bone adhesive 18 through the manipulation surface 16. The thinner LSE sheet 10 may also improve flexing of the LSE sheet 10 when the LSE sheet 10 is peeled from the bone adhesive 18, thereby increasing an initial peel angle $\theta_0$, which may further decrease the LSE adhesive strength 30, shown in FIG. 7, of the LSE sheet 10.

Figure 7:
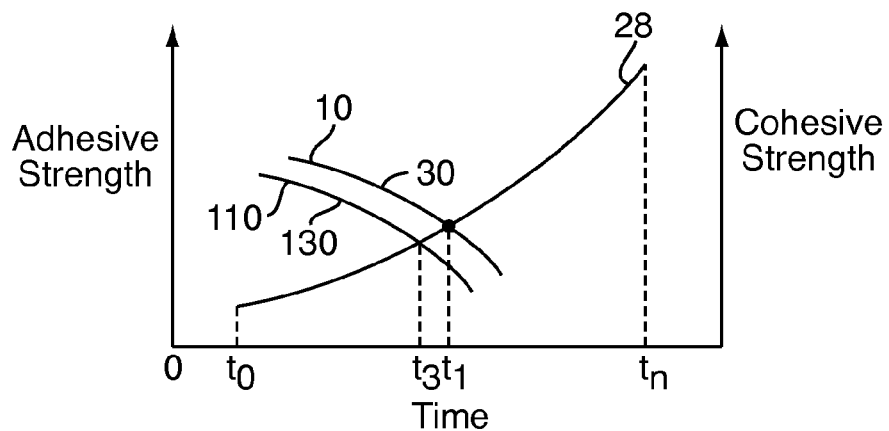
FIG. 7 is a line graph showing a reduction in adhesive strength provided by a low surface energy sheet according to some embodiments of the present invention.

Referring to FIG. 7, wherein like numerals represent like elements, an LSE sheet 110 with a reduced thickness T relative to that of the LSE sheet 10 may have a reduced LSE adhesive strength 130. This reduced LSE adhesive strength 130 may, in turn, lead to a further reduced release time $t_3$ relative to the conventional release time $t_2$, shown in FIG. 3. Thus, reducing the thickness T of the LSE sheet 10 may allow the LSE sheet 110 to be removed from the bone adhesive 18, shown in FIG. 5, after less curing time than the LSE sheet 10. Accordingly, decreasing the thickness T of the LSE sheet 110 may further reduce operating room time for performing bone repair surgeries, resulting in additional time and cost savings relative to those associated with conventional bone adhesives.

However, it should be understood by those skilled in the art that the thickness T of the LSE sheet 10 may be varied from a thin flexible sheet to a thicker less flexible sheet depending upon the desired application. Preferably, the thickness T of the LSE sheet 10 is approximately twenty-five hundredths of a millimeter (0.25 mm). However, as should be recognized by one skilled in the art, the thickness T of the LSE sheet 10 may be increased or decreased depending upon the desired characteristics, e.g., flexibility, size and strength, of the LSE sheet 10 and/or depending upon the intended application for the LSE sheet 10. Additionally, the material forming the LSE sheet 10 preferably has a relatively high elasticity, since for a given thickness T of LSE sheet 10, a more elastic material will release more easily from the bone adhesive 18 than a more rigid material will, due to local flexibility of the LSE sheet 10 at the release point.

Figure 8:
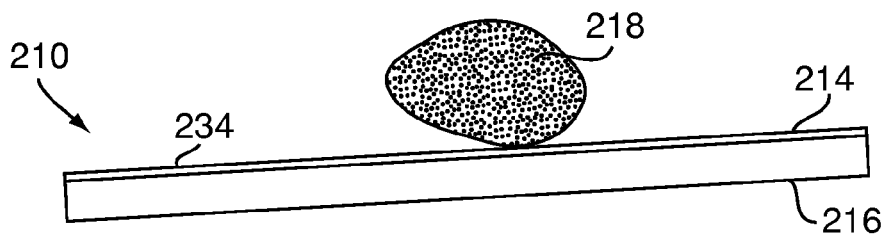
FIG. 8 is a side view of another embodiment of a low surface energy sheet according to the present invention.

Referring to FIG. 8, in some embodiments, the LSE sheet 210 may be provided with a surface coating 234 at the application surface 214 that provides the application surface 214 with the decreased surface energy. The surface coating 234 may be a coating that is chemically bonded to the pliable structure 212 of the LSE sheet 210, such as a surfactant. Alternatively, the surface coating 234 may be a coating that is maintained through an electrostatic charge, such as a powder. Providing the LSE sheet 210 with the surface coating 234 may be particularly beneficial where forming the pliable structure 212 from one of the low surface energy materials discussed above is not possible or in applications where a more rigid LSE sheet 210 is desired. Additionally, as should be understood by those skilled in the art, in some embodiments, it may be desirable to include the surface coating 234 on a highly flexible the LSE sheet 210 formed from one of the low surface energy materials to further reduce the release time $t_1$, shown in FIG. 3.

Although the LSE sheet 10 is shown as being substantially square shaped in FIG. 1A, it should be understood that the LSE sheet 10 may be formed to a variety of different shapes and/or sizes to better suit the LSE sheet 10 for different applications. For instance, the LSE sheet 10 may be formed to be rectangular, triangular, round or any other shape to suit a particular application. Additionally, the LSE sheet 10 may be formed such that the application surface 14 has a surface area as small as approximately one square centimeter (1 cm$^2$) to as large as approximately one hundred square centimeters (100 cm$^2$) depending upon the intended application for the LSE sheet 10.

Figure 9:
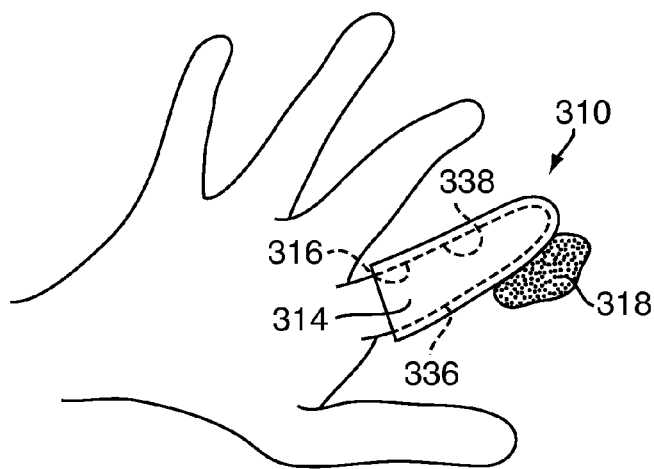
FIG. 9 is a top view of a further embodiment of a low surface energy sheet according to the present invention.

Referring to FIG. 9, in some embodiments, the LSE sheet 310 may be shaped as a sleeve for a user's finger 336. The sleeve shaped LSE sheet 310 may include an internal cavity 338 surrounded by the manipulation surface 316 and adapted to accommodate the user's finger 336. An outer surface of the sleeve shaped LSE sheet 310 forms the application surface 314. Thus, the user is able to shape and/or manipulate bone adhesive 318 disposed on or in contact with the application surface 314 using the finger 336 within the internal cavity 338 of the LSE sheet 310. Then, when the user is finished applying the bone adhesive 318, the user may simply remove the sleeve shaped LSE sheet 310 from the finger 336 to be left with a clean hand or surgical glove. It should be understood by those skilled in the art that multiple sleeve shaped LSE sheets 310 may be used simultaneously to protect multiple fingers 336 from contact with the bone adhesive 318 or multiple sleeve shaped LSE sheets 310 may be formed integrally to provide the user with a glove shaped LSE sheet (not shown).

Figure 10:
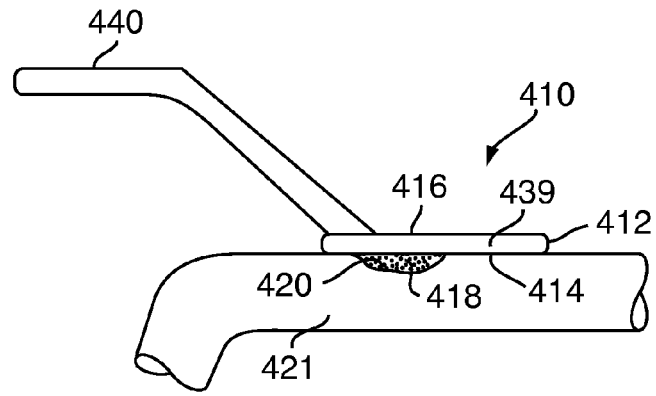
FIG. 10 is a side view of yet another embodiment of a low surface energy sheet according to the present invention.

Referring to FIG. 10, in some embodiments, the LSE sheet 410 may have a relatively rigid structure 439 and may be provided with a handle 440 connected to the manipulation surface 416 to protect the user's hand from contact with the bone adhesive 418. The relatively rigid structure 439 may be formed, for example, by coating a rigid material such as a metal with a material having a low surface energy. In these embodiments, the user may apply, manipulate and/or shape the bone adhesive 418 without directly contacting the bond adhesive 418 using the handle 440. Thus, the user is left with clean hands and/or surgical gloves when done applying and/or manipulating the bone adhesive 418.

Figure 11:
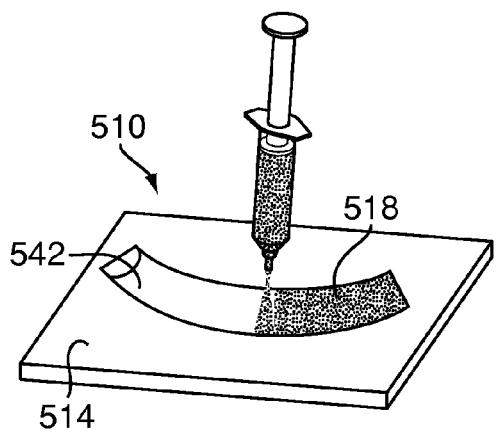
FIG. 11 is a top perspective view of a low surface energy sheet according to a further embodiment of the present invention.

Referring to FIG. 11, in another embodiment, the LSE sheet 510 may be provided with at least one mold cavity 542 formed in the application surface 514. The mold cavity 542 may be formed in a variety of shapes and is preferably formed in the shape of a portion of bone 21, shown in FIG. 1B, that is to be replaced. For example, the mold cavity 542 may be formed in the shape of a patient's rib. In operation, the user may pour or inject the bone adhesive 518 into the mold cavity 542 and allow the bone adhesive 518 to partially cure or polymerize, for example, the user may allow the bone adhesive 518 to cure within the mold cavity 542 for the predetermined release time $t_1$, shown in FIG. 3.

Figure 12:
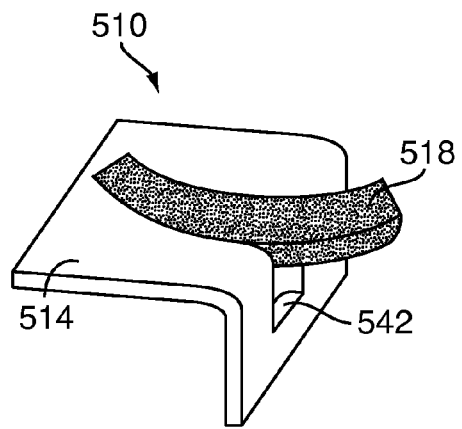
FIG. 12 is a top perspective view of the low surface energy sheet of FIG. 11 with bone adhesive being released therefrom.

Referring to FIG. 12, the user may then release the partially polymerized bone adhesive 518 from the mold cavity 542 by peeling the LSE sheet 510 away from the partially polymerized bone adhesive 518. Since the bone adhesive 518 has partially cured, its cohesive strength 28, shown in FIG. 3, has increased so that the partially polymerized bone adhesive 518 may substantially maintain its molded shape when removed from the mold cavity 542. Preferably, the bone adhesive 518 is still, at least somewhat, chemically adhesive when removed from the LSE sheet 510 so that the bone adhesive 518 may form an adhesive bond with the patient's bone 21, shown in FIG. 1B, and/or another portion of bone adhesive 18.

Once the user has removed the partially polymerized bone adhesive 518 from the LSE sheet 510, the user may place the partially polymerized bone adhesive 518 into the bone defect 20, shown in FIG. 4. In some embodiments, the user may cut the partially polymerized bone adhesive 518 to a desired length after removing the partially polymerized bone adhesive 518 from the mold cavity 542. For example, the user may cut the rib shaped partially polymerized bone adhesive 518 to the length of a corresponding defect in a patient's own rib. The user may then place the cut partially polymerized bone adhesive 518 in the defect and press the ends against exposed bone 21, shown in FIG. 1B, to form the adhesive interface with the bone 21, shown in FIG. 1B. This embodiment of the LSE sheet 510 may be particularly beneficial in applications where bone adhesives 518 of specific shapes and/or sizes are desired.

Figure 13:
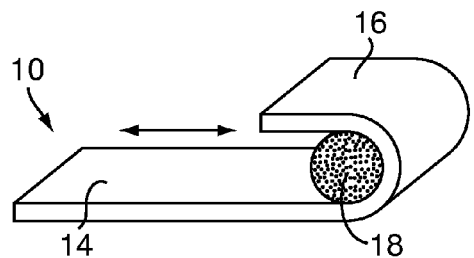
FIG. 13 is a side perspective view of the low surface energy sheet of FIG. 1A being used to manipulate bone adhesive according to another embodiment of the present invention.

Referring to FIG. 13, in some embodiments, where bone adhesive 18 of a particular shape is desired, the user may shape the bone adhesive 18 using the substantially flat LSE sheet 10. For instance, after the bone adhesive 18 is deposited on the application surface 14, the user may shape the bone adhesive 18 through the manipulation surface 16. For example, the user may roll the LSE sheet 10 to form the bone adhesive 18 into a cylindrical shape.

In some embodiments, the user may also mix a second material with the bone adhesive 18 in a similar manner. For instance, the user may deposit the second material on the application surface 14 along with the bone adhesive 18 and then manipulate the LSE sheet 10 through the manipulation surface 16 to mix the second material with the bone adhesive 18. The second material may be, for example, allograft bone, autograft bone, antibiotics, stem cells, a structural feature such as fibers, granules made from the same material as the bone adhesive 18, collagen sponge or the like. Although describes as using a single LSE sheet 10 to mix the second material with the bone adhesive 18, it should be understood by those skilled in the art that a second LSE sheet 10 may be used, thereby allowing the second material and the bone adhesive 18 to be mixed between the two LSE sheets 10. Additionally, in some embodiments, it may be desirable to provide an LSE sheet 10 having a particular shape that is conducive to mixing the second material and the bone adhesive 18. For example, the LSE sheet may be formed in a bag-like shape into which the bone adhesive 18 and the second material may be poured and mixed.

Figure 14:
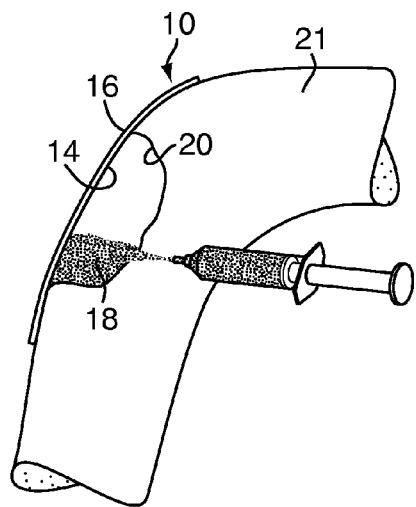
FIG. 14 is a side perspective view of the low surface energy sheet of FIG. 1A being used to deliver bone adhesive to a bone defect according to some embodiments of the present invention.

Referring to FIG. 14, in some embodiments, the LSE sheet 10 may first be positioned over the bone defect 20 and then the bone adhesive 18 may be delivered thereto, for example, by injecting the bone adhesive 18 through a cannula or the like. The LSE sheet 10 may then be maintained in its position until the release time $t_1$, shown in FIG. 3, at which point the LSE sheet 10 may be peeled away from the bone adhesive 18.

Figure 15:
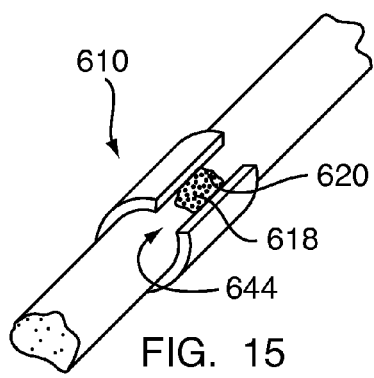
FIG. 15 is a top perspective view of a another embodiment of a low surface energy sheet according to the present invention.

Referring to FIG. 15, in some embodiments, the LSE sheet 610 may be formed in a preset shape to improve positioning of the LSE sheet over the bone defect 620. For instance, the LSE sheet 610 may be formed to be substantially tubular with a longitudinal separation 644 extending the length of the LSE sheet 610. In operation, the LSE sheet 610 may be positioned around the bone defect 620 formed in a somewhat cylindrically shaped bone 21, shown in FIG. 1B, and the LSE sheet 610 may maintain its position thereon, without assistance from the user, due to its tubular shape. Then, the bone defect may be filled with bone adhesive 618 and, after the release time $t_1$, shown in FIG. 3, the LSE sheet 610 may be peeled away from the bone adhesive 618.

Positioning the LSE sheet 10, 610 on the bone defect 20, 620 prior to delivering the bone adhesive 18, 618 is beneficial in that the user does not need to contact the bone adhesive 18, 618 during delivery. These embodiments may be particularly beneficial for applying the bone adhesive 18, 618 while in the substantially liquid state, since the prepositioned LSE sheet 10, 610 may not only shape the bone adhesive 18, 618 as desired, but may also prevent the bone adhesive 18, 618 from migrating out of the bone defect and into the patient's body while in the substantially liquid state. Thus, these embodiments may be particularly advantageous for forming in situ interbody spacers. For example, the LSE sheet 10 may first be positioned within the body where a spine interbody spacer is to be formed. The bone adhesive 18 may then be applied and shaped using the LSE sheet 10 and then the LSE sheet 10 may be peeled away leaving only the interbody spacer behind. These embodiments may also be particularly advantageous for filling a volume between two portions of a fractured bone 21, shown in FIG. 1B, for preventing contamination of the bone adhesive 18 from fluids within the body, such as blood, and/or for preventing the bone adhesive 18, 618 from migrating into the body. For example, the LSE sheet 10 may be positioned below a patient's sternum during a medial sternotomy closure to inhibit bone adhesive 18 from migrating into the patient's chest cavity.

Figure 16:
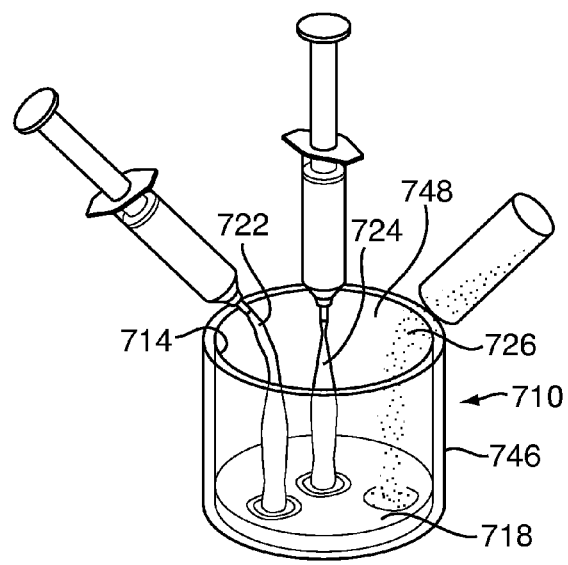
FIG. 16 is a front perspective view of a further embodiment of a low surface energy sheet according to the present invention.

Referring to FIG. 16, in another embodiment, the LSE sheet 710 may form a mixing container 746 for preparing the bone adhesive 718 itself. The mixing container may define an internal mixing cavity 748 that is surrounded by the application surface 714. The prepolymer component 722, polyol component 724 and optional filler material 726 may be combined in the mixing cavity 748 and permitted to react with one another to form the bone adhesive 718. Once the bone adhesive 718 has been formed, the bone adhesive 718 may be deposited on one of the various LSE sheets 10, 110, 210, 310, 410, 510 and 610 discussed above or applied directly to a bone defect 20, 420 and 620, as discussed above. Forming the LSE sheet 710 as the mixing container 746 may advantageously reduce adhesion between the bone adhesive 718 and the mixing container 746, thereby allowing the bone adhesive 718 to be more readily removed from the mixing container 746 and applied to the bone defect 20, shown in FIG. 4, than would be possible with a conventional bone adhesive mixing container.

The bone adhesive application devices and methods of the present invention advantageously allow bone adhesives 18, 218, 318, 418, 518, 618 and 718 with adhesive characteristics to be used in bone repair applications. An advantage of the present invention over conventional bone adhesive application techniques is that the bone adhesive 18, 218, 318, 418, 518, 618 and 718 may be applied to the bone defect 20, 420 and 620 while chemically adhesive to provide a bond between the bone adhesive 18, 218, 318, 418, 518, 618 and 718 and the bone 21, without the bone adhesive 18, 218, 318, 418, 518, 618 and 718 contacting and adhering to undesirable surfaces, such as surgical gloves, bone adhesive holding containers, surgical implantation instruments or the like. Thus, the present invention may provide for a stronger adhesive bond with the bone 21 surrounding the bone defect 20, 420 and 620 than conventional bone application techniques.

The present invention is also advantageous over conventional bone application techniques because the LSE sheet 10, 110, 210, 310, 410, 510, 610 and 710 may act as a barrier preventing contamination of the bone adhesive 18, 218, 318, 418, 518, 618 and 718 during polymerization within the bone defect 20, 420 and 620. Thus, while the present invention discourages bone adhesive contamination, conventional bone adhesive application techniques may themselves contaminate the bone adhesive 18, 218, 318, 418, 518, 618 and 718, thereby causing excessive expansion during polymerization and/or degradation in mechanical properties.

The LSE sheet 10, 110, 210, 310, 410, 510, 610 and 710 is also advantageous over conventional bone adhesive application techniques because it allows the bone adhesive 18, 218, 318, 418, 518, 618 and 718 to be manipulated and shaped within the bone defect 20, 420 and 620. Additionally, the LSE sheet 10, 110, 210, 310, 410, 510, 610 and 710 may advantageously prevent the bone adhesive 18, 218, 318, 418, 518, 618 and 718 from flowing out of the bone defect 20, 420 and 620 and/or from losing its intended shape.

The LSE sheet 10, 110, 210, 310, 410, 510, 610 and 710 of the present invention also advantageously allows bone adhesive application devices to be removed from contact with the bone adhesive 18, 218, 318, 418, 518, 618 and 718 more quickly than conventional devices, which may reduce operating room time for performing bone repair surgeries, resulting in significant time and cost savings.

Although this invention has been shown and described with respect to the detailed embodiments thereof, it will be understood by those skilled in the art that various changes in form and detail thereof may be made without departing from the spirit and the scope of the invention.

What is claimed is:

1. A method for applying a reactive biocompatible polymeric material to a bone defect, said polymeric material having adhesive characteristics and formed by combining a diisocyanate component and a polyol component to form a biocompatible polyurethane material, said polymeric material being initially in a liquid state and passing through a taffy-like state as it cures into its full cured solid state, the method comprising:
   (1) delivering the polymeric material to the bone defect when the polymeric material is in its liquid or taffy-like state;
   (2) positioning a bone adhesive application device over at least a portion of the bone defect and in contact with the polymeric material, said device having an application surface with a surface energy that is the same or less than the surface energy of the polymeric material;
   (3) allowing the polymeric material to at least partially polymerize; and
   (4) removing the device from contact with the polymeric material, prior to complete polymerization when the polymeric material has cured to a sufficient strength to substantially maintain its shape.

2. A method for applying a reactive biocompatible polymeric material to a bone defect, said polymeric material having adhesive characteristics and formed by combining a diisocyanate component and a polyol component to form a biocompatible polyurethane material, said polymeric material being initially in a liquid state and passing through a taffy-like state as it cures into its full cured solid state, the method comprising:
   (1) delivering the polymeric material to the bone defect when the polymeric material is in its liquid or taffy-like state;
   (2) positioning a bone adhesive application device over at least a portion of the bone defect and in contact with the polymeric material, said device having an application surface with a surface energy that is the same or less than the surface energy of the polymeric material;
   (3) allowing the polymeric material to at least partially polymerize; and
   (4) removing the device from contact with the polymeric material, while the polymeric material is still tacky.

3. The method according to claim 1 or 2, wherein the polymeric material is delivered to the bone defect after positioning the device over at least a portion of the bone defect.

4. The method according to claim 1 or 2, further comprising depositing the polymeric material on the application surface of the device.

5. The method according to claim 4, wherein the polymeric material is delivered to the bone defect by positioning the device over the portion of the bone defect.

6. The method according to claim 4, wherein the polymeric material is deposited in a mold cavity of the application surface.

7. The method according to claim 1 or 2, additionally comprising forming the polymeric material in a mixing container having an internal mixing cavity surrounded by an application surface having a surface energy that is the same or less than the surface energy of the polymeric material.

8. The method of claim 1 or 2, wherein the device has a structure that is pliable.

9. The method of claim 8, wherein the device is formed from a material having a low surface energy (LSE) in the form of a thin sheet.

10. The method of claim 9, wherein the LSE sheet is formed from a material comprising polytetrafluoroetheylene, polypropylene, polyethylene terephthalate, and/or polystyrene.

11. The method of claim 9, wherein the LSE sheet is formed from silicone.

12. The method of claim 1 or 2, wherein the polymeric material is formed by combining a diisocyanate component and a polyol component with a filler material to form a biocompatible polyurethane material.

13. The method of claim 12, wherein the filler material is selected from the group consisting of calcium carbonate, bone, calcium phosphate, calcium pyrophosphate, hydroxyapatite, poly methyl methacrylate, glass ionomer, calcium sulfate, tricalcium phosphate, and combinations thereof.

14. The method of claim 1 or 2, wherein the application surface of the device comprises a surface coating that reduces the surface energy of the application surface.

15. The method according to claim 1 or 2, wherein the polymeric material is delivered to the bone defect prior to positioning the device over at least a portion of the bone defect.

16. A method for repairing a bone defect, the method comprising:
  (1) preparing the bone defect to receive a reactive biocompatible polymeric material, said polymeric material having adhesive characteristics and formed by combining a diisocyanate component and a polyol component to form a biocompatible polyurethane material, said polymeric material being initially in a liquid state and passing through a taffy-like state as it cures into its fully cured solid state;
  (2) filling the bone defect with the polymeric material when the polymeric material is in its liquid or taffy-like state; and
  (3) covering the bone defect and polymeric material with a bone adhesive application device wherein said device has an application surface with a surface energy that is the same or less than the surface energy of the polymeric material and wherein said device is impervious to fluids, thereby preventing bodily and surgical fluids from contacting the bone adhesive during polymerization, and
  (4) removing the device from contact with the polymeric material prior to complete polymerization when the polymeric material has cured to a sufficient strength to substantially maintain its shape.

17. The method according to claim 16, additionally comprising shaping the polymeric material through the device.

18. The method according to claim 16, additionally comprising forming the polymeric material by combining a diisocyanate component and a polyol component with a filler material to form a biocompatible polyurethane material, said polymeric material being initially in a liquid state and passing through a taffy-like state as it cures into its fully cured solid state.

\* \* \* \* \*